US008697909B2

(12) United States Patent
Limbach et al.

(10) Patent No.: US 8,697,909 B2
(45) Date of Patent: Apr. 15, 2014

(54) PREPARATION OF α,β-ETHYLENICALLY UNSATURATED CARBOXYLIC SALTS BY CATALYTIC CARBOXYLATION OF ALKENES

(71) Applicant: BASF SE, Ludwigshafen (DE)

(72) Inventors: Michael Limbach, Worms (DE); Ronald Lindner, Dossenheim (DE); Michael Ludwik Lejkowski, Mannheim (DE); Takeharu Kageyama, Hyogo (JP); Gabriella Eva Bodizs, Zürich (CH); Stephan Schunk, Heidelberg (DE); Cornelia Futter, Heidelberg (DE); Jörg Rother, Bruchsal (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/728,081

(22) Filed: Dec. 27, 2012

(65) Prior Publication Data

US 2013/0172616 A1 Jul. 4, 2013

Related U.S. Application Data

(60) Provisional application No. 61/581,111, filed on Dec. 29, 2011.

(51) Int. Cl.
*C07C 51/15* (2006.01)
(52) U.S. Cl.
USPC .......................................... 562/550
(58) Field of Classification Search
None
See application file for complete search history.

(56) References Cited

U.S. PATENT DOCUMENTS

| 4,435,598 A | 3/1984 | Hinnenkamp |
| 2009/0299094 A1 | 12/2009 | Fukuda et al. |
| 2011/0218359 A1 | 9/2011 | Limbach et al. |
| 2012/0029243 A1 | 2/2012 | Pantouflas et al. |
| 2012/0165588 A1 | 6/2012 | Dehn et al. |
| 2012/0302786 A1 | 11/2012 | Stroefer et al. |
| 2013/0018205 A1 | 1/2013 | Teles et al. |

FOREIGN PATENT DOCUMENTS

WO   WO-2011/107559   9/2011

OTHER PUBLICATIONS

Fischer et al., Chem. Comm., 2006, 2510-2512.*
Graham et al., Organometallics, 2007, 26, 6784-6792.*
Bruckmeier et al., Organometallics, 2010, 29, 2199-2202.*

(Continued)

*Primary Examiner* — Karl J Puttlitz
(74) *Attorney, Agent, or Firm* — Servilla Whitney LLC

(57) ABSTRACT

In a process for preparing an alkali metal or alkaline earth metal salt of an α,β-ethylenically unsaturated carboxylic acid, a) a transition metal-alkene complex is reacted with $CO_2$ to give a metallalactone, b) the metallalactone is reacted with a base to give an adduct of the alkali metal or alkaline earth metal salt of the α,β-ethylenically unsaturated carboxylic acid with the transition metal complex, and c) the adduct is reacted with an alkene to release the alkali metal or alkaline earth metal salt of the α,β-ethylenically unsaturated carboxylic acid and regenerate the transition metal-alkene complex. The base is selected from alkali metal or alkaline earth metal hydroxides and alkali metal or alkaline earth metal superbases. The alkene is, for example, ethene. The transition metal complex comprises, for example, nickel and a bidentate P,P, P,N, P,O or P,carbene ligand, such as 1,2-bis(di-tert-butylphosphino)ethane.

14 Claims, 2 Drawing Sheets

(56) References Cited

OTHER PUBLICATIONS

Anderson, John S. et al., "Reactions of CO2 and CS2 with 1,2-Bis(di-tert-butylphosphino)ethane Complexes of Nickel(0) and Nickel(1)", *Inorg. Chem*, 49 2010, 10203-10207.

Aresta, Michele et al., "(Carbon dioxide)bis(trialkylphosphine)nickel Complexes", *J. Chem Soc J.C.S. Dalton* 1977, 708-711.

Bruckmeier, Christian et al., "Formation of Methyl Acrylate from CO2 and Ethylene via Methylation of Nickelalactones", *Organometallics*, 29 2010, 2199-2202.

Graham, David C. et al., "Production of Acrylic Acid through Nickel-Mediated Coupling of Ethylene and Carbon Dioxide—A DFT Study", *Organometallics*, 26 2007, 6784-6792.

Hoberg, Heinz et al., "A 1-Oxa-2-nickela-5-cyclopentanone from Ethene and Carbon Dioxide: Preparation, Structure and Reactivity", *Angew. Chem. Int. Ed. Engl.* 16, No. 8 1987, 771-773.

Hoberg, Heinz et al., "Nickel(0)-Induzierte C-C-Verknupfung Zwischen Alkenen Und Kohlendioxid", *Journal of Organometallic Chemistry* 236 1982, C28-C30.

Hoberg, Heinz et al., "Nickel(0)-Induzierte C-C-Verknupfung Zwischen Kohlendioxid und Ethylen Sowie Mono-Oder Di-Substituierten Alkenen", *Organomet. Chem.* 251(3) 1983, C51-C53.

Langer, Jens et al., "Low-Valent Nickel and Palladium Complexes with 1,1'-Bis(phosphanyl)-ferrocenes: Syntheses and Structures of Acrylic Acid and Ethylene Complexes", *Eur. J. Inorg. Chem.* 2007, 2257-2264.

Lee, S. Y. et al., "Transformation of Nickelalactones to Methyl Acrylate: On the Way to a Catalytic Conversion of Carbon Dioxide", *ChemSusCham* 4 2011, 1275-1279.

Yamamoto, Takakazu et al., "Preparation and Properties of Phosphine Complexes of Nickel-Containing Cyclic Amides and Esters", *J. Am. Chem. Soc.* 102 1980, 7448-7456.

PCT International Search Report in PCT/IB2012/057750 dated May 30, 2013, 4 pgs.

Hoberg, Heinz et al., "C-C-Verknupfung Von Alkenen Mit CO2 an Nickel(0); Herstellung Von Zimtsaure Aus Stryol", *Journal of Organometallic Chemistry*, 307 1986, C38-C40.

\* cited by examiner

PREPARATION OF α,β-ETHYLENICALLY UNSATURATED CARBOXYLIC SALTS BY CATALYTIC CARBOXYLATION OF ALKENES

CROSS-REFERENCE TO RELATED APPLICATIONS

This application claims the benefit under 35 U.S.C. §119 (e) to U.S. Provisional Application No. 61/581,111, filed Dec. 29, 2011, the entire content of which is incorporated herein by reference in its entirety

FIELD

Embodiments of the present invention generally relate to processes for preparing an alkali metal or alkaline earth metal salt of an α,β-ethylenically unsaturated carboxylic acid.

BACKGROUND

The direct addition of $CO_2$ onto ethylene to give acrylic acid (scheme 1) is industrially unattractive due to thermodynamic limitations ($\Delta G=34.5$ kJ/mol) and the unfavorable equilibrium, which at room temperature is virtually completely to the side of the reactants ($K_{293}=7\times10^{-7}$).

Scheme 1:

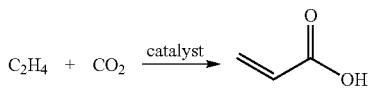

By using a base, it is possible to convert the α,β-ethylenically unsaturated acid to the salt thereof and thus to shift the equilibrium to the side of the products. The reaction, however, is kinetically inhibited and therefore requires a homogeneous or heterogeneous carboxylation catalyst.

According to Aresta et al. (*J. Chem. Soc., Dalton Trans.* 1977, 7, 708) and Hillhouse et al. (*Inorg. Chem.* 2010, 49, 10203), a ligand and a homogeneous Ni(0) species such as bis(1,5-cyclooctadiene)nickel ($Ni(COD)_2$) in the presence of $CO_2$ readily form a ligand-Ni—$CO_2$ adduct (scheme 2), which is thermally labile, and one way in which it decomposes is with oxidation of the ligand, even at low temperatures of 80° C. This is disadvantageous since the potential catalyst or precursors thereof are thus degraded.

Scheme 2:

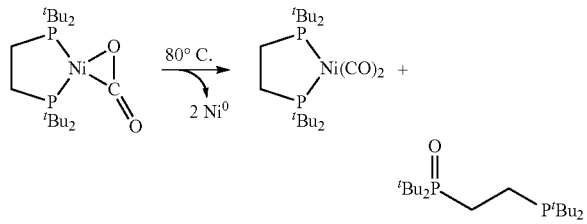

According to Yamamoto et al. (*J. Am. Chem. Soc.* 1980, 102, 7448), the equimolar reaction of acrylic acid with $Ni(COD)_2$ in the presence of a tertiary phosphine ligand at temperatures above 0° C. gives rise to the stable five-membered nickelalactone ring A, called the Hoberg complex (scheme 3). At temperatures below 0° C., the same reaction gives an equimolar mixture of the lactone A and of the open-chain π-complex B. The thermal cleavage of A or of the mixture A/B to give free acrylic acid did not succeed. An equilibrium between A and B, which is an important prerequisite for a catalytic transformation, was likewise postulated by Walther et al., but not observed experimentally (*Eur. J. Inorg. Chem.* 2007, 2257).

Scheme 3:

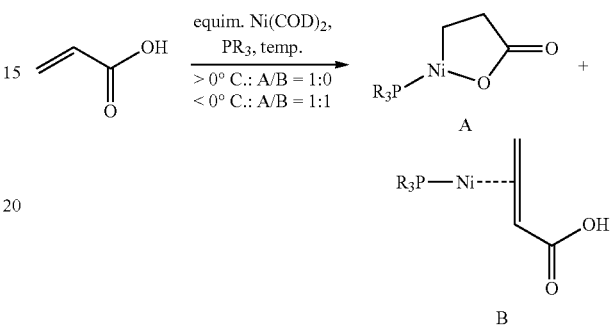

Nickelalactones A may bear one or more ligands and arise from the direct and stoichiometric coupling of $CO_2$ and ethylene, as found by Hoberg (*J. Organomet. Chem.* 1983, C51). The reaction was performed at industrially unfavorable temperatures of down to −70° C. (*J. Organomet. Chem.* 1982, 236, C28; *Angew. Chem. Int. Ed. Engl.* 1987, 26, 771). In addition, for example, the nickelalactones which originate from the reaction of the basic 2,2'-bipyridine ligand, an Ni(0) species, alkenes and $CO_2$ are isolable as stable solids (*J. Organomet. Chem.* 1982, C28), which demonstrates the exceptional stability of these compounds.

The treatment of such stable nickelalactones with aqueous mineral acids gives rise to the saturated acid propionic acid, but not acrylic acid. This suggests that the β-hydride elimination needed to form acrylic acid and derivatives thereof from the complex A is difficult. Accordingly, there has still been no description of a catalytic variant of this reaction.

This suggestion is supported by quantum-mechanical studies by Buntine et al. These show the increase in stability by ~40 kcal/mol of the intermediate nickelalactone bearing two DBU ligands compared to the desired acrylic acid elimination product (*Organometallics* 2007, 26, 6784).

Rieger et al. have for the first time successively released an acrylic acid derivative from a nickelalactone by reaction with methyl iodide or with LiI. The transformation gives, as well as methyl propionate, which indicates an unproductive decomposition of the nickelalactone, low yields of methyl acrylate (max. 33%); no catalysis cycle was described. In the case of use of LiI, at best only traces of methyl acrylate were found. The nickelalactones used bear the ligands diphenylphosphinopropane (dppp), diphenylphosphinoethane (dppe) and tetramethylethylenediamine (TMEDA). The two former lactones were prepared by ligand exchange of the lactone prepared from $Ni(COD)_2$, TMEDA and succinic anhydride, and none of the lactones were synthesized proceeding from $CO_2$ and ethylene in a one-pot reaction (*Organometallics* 2010, 29, 2199).

Similar results in principle, with better yields, were found by Herrmann and Kühn et al. (*ChemSusChem* 2011, 4, 1275-1279). There was no description of a catalytic reaction regime here either.

WO 2011/107559 discloses a process for preparing an alkali metal or alkaline earth metal salt of an α,β-ethylenically unsaturated carboxylic acid, wherein a) an alkene, $CO_2$ and a carboxylation catalyst are converted to an alkene/$CO_2$/carboxylation catalyst adduct, b) the adduct is decomposed to release the carboxylation catalyst with an auxiliary base to give the auxiliary base salt of the α,β-ethylenically unsaturated carboxylic acid, c) the auxiliary base salt of the α,β-ethylenically unsaturated carboxylic acid is reacted to release the auxiliary base with an alkali metal or alkaline earth metal base to give the alkali metal or alkaline earth metal salt of the α,β-ethylenically unsaturated carboxylic acid. The process achieves the cleavage of the intermediate adduct by means of an auxiliary base, for example of a tertiary amine, in order to prepare, in a first step, the ammonium salt of the α,β-ethylenically unsaturated carboxylic acid, which overcomes the fundamental thermodynamic limitation. In a second step, for example with aqueous sodium hydroxide solution, the ammonium cation is exchanged for sodium, in order thus to obtain the sodium salt of the α,β-ethylenically unsaturated carboxylic acid. This two-stage reaction regime is complex. Moreover, the cleavage of the lactone is slow and thus reduces the space-time yield of such a process considerably.

SUMMARY

Embodiments of the present invention relate to a process for preparing an alkali metal or alkaline earth metal salt of an α,β-ethylenically unsaturated carboxylic acid by catalytic carboxylation of alkenes. More particularly, one or more embodiments of the invention relate to a process for preparing sodium acrylate by direct carboxylation of ethene with carbon dioxide ($CO_2$). Acrylic acid and derivatives thereof are important industrial chemicals and monomer units for production of water-absorbing resins, called superabsorbents.

DETAILED DESCRIPTION

Embodiments of the invention provide a process for preparing an alkali metal or alkaline earth metal salt of an α,β-ethylenically unsaturated carboxylic acid, wherein
a) a transition metal-alkene complex is reacted with $CO_2$ to give a metallalactone,
b) the metallalactone is reacted with a base to give an adduct of the alkali metal or alkaline earth metal salt of the α,β-ethylenically unsaturated carboxylic acid with the transition metal complex, the base being selected from alkali metal or alkaline earth metal hydroxides and alkali metal or alkaline earth metal superbases, and
c) the adduct is reacted with an alkene to release the alkali metal or alkaline earth metal salt of the α,β-ethylenically unsaturated carboxylic acid and regenerate the transition metal-alkene complex.

In step c), the transition metal-alkene complex may be regenerated and may be available again for step a). This completes the catalytic cycle.

In some embodiments, the catalytic process is suitable for industrial preparation of α/β-ethylenically unsaturated carboxylic acid derivatives from $CO_2$ and an alkene.

The term "transition metal complex" used in the present application comprises, in a generic manner, all transition metal complexes through which a catalytic cycle passes, especially the transition metal-alkene complex, the metallalactone and the adduct of the alkali metal or alkaline earth metal salt of the α,β-ethylenically unsaturated carboxylic acid with the transition metal complex.

The expression "transition metal-alkene complex" should be interpreted broadly and describes any possible coordination known to those skilled in the art of alkenes to transition metal centers. The transition metal-alkene complex can be illustrated by the general formula I

in which
M is a transition metal,
L is a ligand,
n is 1 or 2,
$R^a$, $R^b$ and $R^c$ are each independently hydrogen, $C_{1-12}$-alkyl, $C_{2-12}$-alkenyl, or $R^a$ and $R^b$ together with the carbon atoms to which they are bonded are a mono- or diethylenically unsaturated, 5- to 8-membered carbocycle.

In one or more embodiments, M is an active metal as defined below, such as nickel, iron or rhodium. In some embodiments, M is nickel.

In one or more embodiments, L is a ligand as defined below.

In some embodiments, $R^c$ is hydrogen; $R^b$ and $R^c$ are each hydrogen; or $R^a$, $R^b$ and $R^c$ are each hydrogen.

The expression "transition metal-alkene complex" shall comprise isolable and unstable intermediates of the general formula I.

The expression "metallalactone" denotes, according to the exchange nomenclature ("a" nomenclature), a lactone (γ-lactone) in which a carbon atom has been exchanged for a metal atom. The expression "metallalactone" should be interpreted broadly and may comprise compounds with structures similar to the Hoberg complex mentioned at the outset, or related compounds of oligomeric or polymeric structure. The expression shall comprise isolable compounds and (unstable) intermediates.

The metallalactone can be illustrated by the general formula II

in which M, L, n, $R^a$, $R^b$ and $R^c$ are each as already defined.

The formation of the adduct of the alkali metal or alkaline earth metal salt of the α,β-ethylenically unsaturated carboxylic acid with the transition metal complex probably proceeds via an intermediate of the general formula III

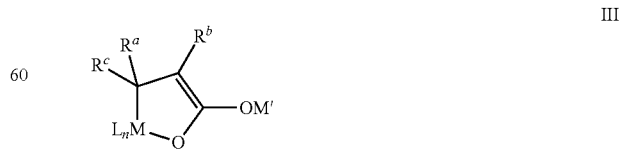

in which M, L, n, $R^a$, $R^b$ and $R^c$ are each as already defined and M' is an alkali metal or the equivalent of an alkaline earth metal.

The adduct of the alkali metal or alkaline earth metal salt of the α,β-ethylenically unsaturated carboxylic acid with the transition metal complex can be illustrated by the general formula IV

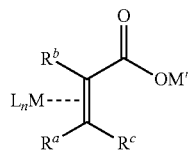

IV in which M, L, n, M', $R^a$, $R^b$ and $R^c$ are each as already defined.

In general, the transition metal complex comprises, as the active metal, at least one element of groups 4 (such as Ti, Zr), 6 (such as Cr, Mo, W), 7 (such as Re), 8 (such as Fe, Ru), 9 (such as Co, Rh) and 10 (such as Ni, Pd, Pt) of the Periodic Table of the Elements. In one or more embodiments, the metal is nickel, cobalt, iron, rhodium, ruthenium, palladium, platinum, rhenium, tungsten. In some embodiments, the metal is nickel, palladium, platinum, cobalt, iron, rhodium, ruthenium. In some embodiments, the transition metal complex comprises a complex of nickel, iron or rhodium. In some embodiments, the transition metal complex comprises a complex of nickel or palladium.

The role of the active metal consists in the activation of $CO_2$ and alkene in order to form a C—C bond between $CO_2$ and the alkene.

The transition metal-alkene complex comprises a ligand L. The ligand stabilizes the metallalactone formed from the transition metal-alkene complex. The ligand is selected such that it leaves coordination sites for the alkene and $CO_2$ unoccupied on the metal.

The ligand may be monodentate or polydentate, for example bidentate. In general, a suitable monodentate ligand coordinates twice (n=2), and a bidentate ligand once (n=1), to the metal center.

According to one or more embodiments, the polydentate, e.g. bidentate, ligand coordinates to the transition metal to form a five-membered ring, i.e. the transition metal, the atoms which coordinate to the transition metal and the atoms of the shortest chain which connects the atoms coordinating to the transition metal together form a five-membered ring.

The ligand L may comprise at least one phosphorus atom, nitrogen atom, oxygen atom and/or carbene group which coordinates to the transition metal. The ligand L may be selected, for example, from phosphines, phosphites, amines and N-heterocyclic carbenes. The ligand L may comprise at least one phosphorus atom and/or carbene group which coordinates to the transition metal. In some embodiments, the ligand L comprises at least one phosphorus atom which coordinates to the transition metal.

In one or more embodiments, when the ligand L comprises at least one phosphorus atom which coordinates to the transition metal, at least one radical may be bonded to the phosphorus atom via a secondary or tertiary carbon atom. More particularly, at least two radicals are bonded to the phosphorus atom via a secondary or tertiary carbon atom. Suitable radicals bonded to the phosphorus atom via a secondary or tertiary carbon atom are, for example, adamantyl, tert-butyl, sec-butyl, isopropyl, phenyl, tolyl, xylyl, mesityl, naphtyl, fluorenyl or anthracenyl, especially tert-butyl or phenyl.

According to one or more embodiments, when the ligand L comprises at least one N-heterocyclic carbene which coordinates to the transition metal, at least one radical may be bonded via a tertiary carbon atom to at least one α-nitrogen atom to the carbene group. Suitable radicals bonded to the nitrogen atom via a tertiary carbon atom are, for example, adamantyl or tert-butyl, especially tert-butyl.

In some embodiments, the ligand is a bidentate P,P, P,N, P,O or P,carbene ligand. The bidentate P,P, P,N, P,O or P,carbene ligand may coordinate to the transition metal to form a five-membered ring.

Suitable monodentate ligands have, for example, the formula V $$WR^1R^2R^3 \qquad\qquad V$$

in which
W is phosphorus (P), phosphite (P=O) or amine (N), and
$R^1$, $R^2$ and $R^3$ are each independently alkyl, cycloalkyl or aryl.

Suitable monodentate ligands are also N-heterocyclic carbenes of the formula VI

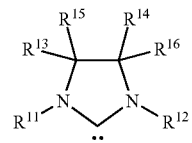

VI in which
$R^{11}$ and $R^{12}$ are each independently alkyl or aryl,
$R^{13}$, $R^{14}$, $R^{15}$ and $R^{16}$ are each independently hydrogen, alkyl or aryl,
or $R^{15}$ and $R^{16}$ together are a chemical bond.

Suitable bidentate ligands L have the general formula VII $$L^1\text{-}(CR^4R^5)_m\text{-}L^2 \qquad\qquad VII$$

in which
$L^1$ is $PR^1R^2$ or $P(O)R^1R^2$,
$L^2$ is $PR^1R^2$, $P(O)R^1R^2$, $NR^1R^2$, $COO^-$,
an N-heterocyclic carbene radical of the formula VIII

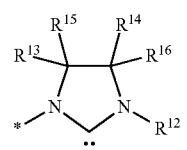

VIII in which * is the bonding site to the rest of the molecule,
$R^{12}$, $R^{13}$, $R^{14}$, $R^{15}$ and $R^{16}$ are each as already defined,
or a pyridine radical of the formula IX

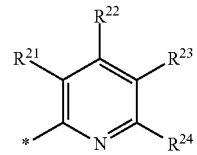

IX in which * is the bonding site to the rest of the molecule,
$R^{21}$, $R^{22}$, $R^{23}$ and $R^{24}$ are each independently hydrogen, alkyl or aryl,
$R^1$ and $R^2$ are each as already defined,
$R^4$ and $R^5$ are each independently hydrogen, alkyl or aryl,
m is 1 or 2.

For the purposes of the present application, the expression "alkyl" comprises straight-chain and branched alkyl groups.

According to one or more embodiments, these may be $C_1$-$C_{20}$-alkyl, $C_1$-$C_{12}$-alkyl, $C_1$-$C_8$-alkyl or $C_1$-$C_4$-alkyl. Examples of alkyl groups are especially methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" comprises unsubstituted and substituted alkyl groups which have generally 1, 2, 3, 4 or 5 substituents. In some embodiments, alkyl groups have 1, 2 or 3 substituents or 1 substituent. In some embodiments, these may be selected from alkoxy, cycloalkyl, aryl, hetaryl, hydroxyl, halogen, $NE^1E^2$, $NE^1E^2E^{3+}$, carboxylate and sulfonate. Some embodiments provide that the perfluoroalkyl group is trifluoromethyl.

The expression "cycloalkyl" comprises monocyclic and polycyclic alkyl groups, especially monocyclic, bicyclic or tricyclic alkyl groups. According to one or more embodiments, they are $C_3$-$C_{20}$-cycloalkyl, $C_4$-$C_{12}$-cycloalkyl, or $C_5$-$C_8$-cycloalkyl.

Examples of alkyl groups are cyclopropyl, cyclobutyl, cyclopentyl, cyclohexyl, cycloheptyl, cyclooctyl or adamantyl. The expression "cycloalkyl" comprises unsubstituted and substituted cycloalkyl groups which have generally 1, 2, 3, 4 or 5. In one or more embodiments, the cycloalkyl group has 1, 2 or 3 substituents or 1 substituent. In some embodiments, these may be selected from alkoxy, aryl, hetaryl, hydroxyl, halogen, $NE^1E^2$, $NE^1E^2E^{3+}$, carboxylate and sulfonate.

The expression "aryl" in the context of the present invention comprises unsubstituted and also substituted aryl groups. In one or more embodiments, the aryl group is $C_6$-$C_{18}$-aryl, such as phenyl, tolyl, xylyl, mesityl, naphthyl, fluorenyl, anthracenyl, phenanthrenyl or naphthacenyl, particularly phenyl or naphthyl, where these aryl groups in the case of substitution may bear generally 1, 2, 3, 4 or 5 substituents, 1, 2 or 3 substituents, or 1 substituent, selected from the alkyl, alkoxy, carboxylate, trifluoromethyl, sulfonate, $NE^1E^2$, alkylene-$NE^1E^2$, nitro, cyano or halogen groups. In some embodiments, the perfluoroaryl group is pentafluorophenyl.

Carboxylate and sulfonate in the context of this invention may be a derivative of a carboxylic function and of a sulfonic acid function respectively, especially a metal carboxylate or sulfonate, a carboxylic ester or sulfonic ester function, or a carboxamide or sulfonamide function. Examples of these include the esters with $C_1$-$C_4$-alkanols, such as methanol, ethanol, n-propanol, isopropanol, n-butanol, sec-butanol and tert-butanol.

The above explanations regarding the expressions "alkyl" and "aryl" apply correspondingly to the expressions "alkoxy" and "aryloxy".

The $E^1$, $E^2$ and $E^3$ radicals are each independently selected from hydrogen, alkyl, cycloalkyl and aryl. In one or more embodiments, the $NE^1E^2$ group is N,N-dimethylamino, N,N-diethylamino, N,N-dipropylamino, N,N-diisopropylamino, N,N-di-n-butylamino, N,N-di-tert-butylamino, N,N-dicyclohexylamino or N,N-diphenylamino.

Halogen is fluorine, chlorine, bromine and iodine. In some embodiments, the halogen is fluorine, chlorine or bromine.

According to one or more embodiments, W in the formula V is P.

In some embodiments, in the formula V, at least one radical, especially at least two radicals, of the $R^1$, $R^2$ and $R^3$ radicals is adamantyl, tert-butyl, sec-butyl, isopropyl, phenyl, tolyl, xylyl, mesityl, naphtyl, fluorenyl or anthracenyl, especially tert-butyl or phenyl.

In some embodiments, in the formula VI, $R^{11}$ and $R^{12}$ may each be adamantyl, tea-butyl, sec-butyl, isopropyl, phenyl, tolyl, xylyl, mesityl, naphtyl, fluorenyl or anthracenyl, especially tert-butyl or phenyl.

In some embodiments, in the formula VI, $R^{13}$, $R^{14}$, $R^{15}$ and $R^{16}$ may each independently be hydrogen or alkyl, especially hydrogen or $C_1$-$C_4$-alkyl, particularly hydrogen, or $R^{15}$ and $R^{16}$ together are a chemical bond.

In some embodiments, in the formula VII, $L^1$ may be $PR^1R^2$. $L^2$ may be $PR^1R^2$, an N-heterocyclic carbene radical of the formula VIII or a pyridine radical of the formula IX. In some embodiments, $L^1$ and $L^2$ are each $PR^1R^2$.

In some embodiments, in the formula VII, $R^4$ and $R^5$ may each independently be hydrogen or $C_1$-$C_4$-alkyl; more particularly, $(CR^4R^5)_m$ is —$CH_2$— or —$CH_2$—$CH_2$—.

In some embodiments, in the formula VII, at least one radical of the $R^1$ and $R^2$ radicals, especially both of the $R^1$ and $R^2$ radicals, (per phosphorus atom) is adamantyl, tert-butyl, sec-butyl, isopropyl, phenyl, tolyl, xylyl, mesityl, naphtyl, fluorenyl or anthracenyl, especially tert-butyl or phenyl.

In some embodiments, in the formula VIII, $R^{12}$ is adamantyl, tert-butyl, sec-butyl, isopropyl, phenyl, tolyl, xylyl, mesityl, naphtyl, fluorenyl or anthracenyl, especially tert-butyl or phenyl.

In some embodiments, in the formula VIII, $R^{13}$, $R^{14}$, $R^{15}$ and $R^{16}$ are each independently hydrogen or alkyl, especially hydrogen or $C_1$-$C_4$-alkyl, particularly hydrogen, or $R^{15}$ and $R^{16}$ together are a chemical bond.

In some embodiments, the ligand having formula VII may be:
2-(diphenylphosphino)acetate,
2-(dimethylphosphino)-N,N-dimethylethaneamine,
1,2-bis(di-tert-butylphosphino)ethane,
bis(di-tert-butylphosphino)methane,
2-(2-(diphenylphosphino)ethyl)pyridine or
3-tert-butyl-1-(di-tert-butylphosphinomethyl)imidazol-2-ylidene.

In one or more embodiments, the ligand is 1,2-bis(Di-tert-butylphosphino)ethane or bis(di-tert-butylphosphino)methane.

In addition, at least one equivalent of the anion from the base may itself function as a ligand on the metal of the transition metal complex.

In addition to the above-described ligands, the transition metal complex may also have at least one further ligand selected from halides, amines, amides, oxides, phosphides, carboxylates, acetylacetonate, aryl- or alkylsulfonates, hydride, CO, olefins, dienes, cycloolefins, nitriles, aromatics and heteroaromatics, ethers, $PF_3$, phospholes, phosphabenzenes, and mono-, di- and polydentate phosphinite, phosphonite, phosphoramidite and phosphite ligands.

Suitable alkenes are those of the formula IX

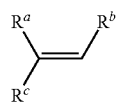

IX in which $R^a$, $R^b$ and $R^c$ are each as already defined.

Suitable alkenes are, for example, ethene, propene, isobutene, butadiene, piperylene, 1-butene, 1-pentene, 1-hexene, 1-heptene, 1-octene, 1-nonene, 1-decene. The alkene to be used in the carboxylation is generally gaseous or liquid under the reaction conditions.

In one or more embodiments, the alkene is ethene. The process according to the invention makes it possible to obtain alkali metal or alkaline earth metal acrylates, especially sodium acrylate.

The transition metal-alkene complex used in step a) can initially be obtained by reacting the alkene and a transition metal precomplex to give the transition metal-alkene complex. The transition metal precomplex comprises a ligand L and may comprise at least one further ligand which can be displaced by the alkene. Alternatively, the transition metal-alkene complex can be obtained initially by reacting a transition metal source with a ligand L and an alkene to give the transition metal-alkene complex.

Useful transition metal sources include commercial standard complexes, for example [M(p-cymene)Cl$_2$]$_2$, [M(benzene)Cl$_2$]$_n$, [M(COD)$_2$], [M(CDT)], [M(C$_2$H$_4$)$_3$], [MCl$_2$×H$_2$O], [MCl$_3$×H$_2$O], [M(acetylacetonate)$_3$], [M(DMSO)$_4$Cl$_2$], where M is as already defined.

In some embodiments, the transition metal-alkene complex, the metallalactone and the adduct of the alkali metal or alkaline earth metal salt of the α,β-ethylenically unsaturated carboxylic acid with the transition metal complex are present in homogeneous solution in the reaction mixture in the form of complex-type compounds.

The solvent selected is one in which the transition metal complex has good solubility. Examples include aromatic hydrocarbons such as benzene, toluene or xylene, halogenated aromatic hydrocarbons such as chlorobenzene, ethers such as tetrahydrofuran, alcohols such as methanol, ethanol, isopropanol, dimethylformamide, dimethyl sulfoxide and water, or any mixtures of these solvents with one another, for example chlorobenzene/methanol or methanol/water.

In some embodiments, the solvent is chlorobenzene.

In step a), the transition metal-alkene complex is reacted with CO$_2$ to give a metallalactone. This involves an insertion of the CO$_2$ into the metal-alkene bond to form a C—C bond to the alkene.

In step b), the metallalactone is reacted with a base to give an adduct of the alkali metal or alkaline earth metal salt of the α,β-ethylenically unsaturated carboxylic acid with the transition metal complex. The base used is selected from alkali metal or alkaline earth metal hydroxides and alkali metal or alkaline earth metal superbases. A superbase is understood to mean a base which reacts on contact with water quantitatively to give hydroxide ions and the corresponding acid of the superbase. In other words, a base whose base strength corresponds to or is higher than that of hydroxide ions is used. The bases used are sufficiently basic to deprotonate the metallalactone in the α position. The alkali metal or alkaline earth metal cation is probably capable, due to its Lewis acidity, of stabilizing the carboxylate group which forms.

The base can be added in solid form or as a solution. In one or more embodiments, a solution of the base is added. The base solvent may be different than or identical to the reaction solvent. In some embodiments, the base solvent is at least partly miscible with the reaction solvent.

According to one or more embodiments, the alkali metal may be selected from lithium, sodium and potassium; more particularly, the alkali metal is sodium. In some embodiments, the alkaline earth metal may be selected from magnesium, calcium, strontium and barium.

Suitable alkali metal hydroxides are, for example, NaOH, KOH or LiOH. In the case of the hydroxides, an aqueous solution of the hydroxide is sufficient. A solubilizer can optionally be added, for example an alcohol.

In one or more embodiments, the alkali metal or alkaline earth metal superbase is selected from alkali metal or alkaline earth metal alkoxides, alkali metal or alkaline earth metal hydrides, alkali metal or alkaline earth metal azides, alkali metal or alkaline earth metal phosphides, alkali metal or alkaline earth metal silanolates, alkali metal or alkaline earth metal alkyls and alkali metal or alkaline earth metal aryls.

Suitable alkali metal or alkaline earth metal alkoxides are C$_{1-16}$-alkoxides, such as C$_{1-12}$-alkoxides, especially C$_{1-4}$-alkoxides. Suitable alkoxides derive from alcohols of the formula R$^{100}$OH. Suitable R$^{100}$ radicals are branched or unbranched, acyclic or cyclic alkyl radicals having 1-16 carbon atoms, such as 1-12 carbon atoms, which are unsubstituted or wherein individual carbon atoms may each independently also be replaced by a heteroatom selected from the group of 0 and >N. Suitable R$^1$ radicals are benzyl, methyl, ethyl, 1-propyl, 2-propyl, 1-butyl, 2-butyl, 2-(2-methyl)propyl, 1-(2-methyl)propyl, 1-(2-methyl)butyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, C$_3$-C$_{10}$-cycloalkyl which is unsubstituted or may bear a C$_1$-C$_4$-alkyl group, for example cyclopentyl, methylcyclopentyl, cyclohexyl, methylcyclohexyl, cycloheptyl, cyclooctyl.

Suitable alkali metal or alkaline earth metal alkoxides are sodium methoxide, sodium ethoxide, sodium isopropoxide, sodium tert-butoxide. In the case of the alkoxides, the alcohol itself may serve as the solvent. In some embodiments, the base is sodium tert-butoxide.

Suitable alkali metal or alkaline earth metal hydrides are, for example, lithium hydride, sodium hydride, potassium hydride, and magnesium hydride, calcium hydride.

Suitable alkali metal or alkaline earth metal amides are LiNMe$_2$, LiNEt$_2$, LiNiPr$_2$, NaNMe$_2$, NaNEt$_2$, NaNiPr$_2$, KNMe$_2$, KNEt$_2$, KNiPr$_2$, LiN(CHMe$_2$)$_2$, NaN(CHMe$_2$)$_2$, KN(CHMe$_2$)$_2$ (Me=Methyl; Et=Ethyl; Pr=Isopropyl). The suitable amides also include silicon-containing amides such as sodium hexamethyldisilazide (NaHMDS), potassium hexamethyldisilazide (KHMDS) or lithium hexamethyldisilazide (LiHMDS).

Suitable alkali metal or alkaline earth metal phosphides are those of the formula MPR$^2$$_2$ in which M is an alkali metal or an equivalent of an alkaline earth metal, and R$^2$ is C$_{1-12}$-alkyl or C$_{6-10}$-aryl, for example KPPh$_2$ (Ph=Phenyl).

Suitable alkali metal or alkaline earth metal silanolates are those of the formula MOSi(C$_{1-4}$-Alkyl)$_3$ in which M is an alkali metal or an equivalent of an alkaline earth metal, for example NaOSiMe$_3$.

Suitable alkali metal or alkaline earth metal alkyls or aryls are lithium alkyl compounds, such as methyllithium, n-butyllithium, sec-butyllithium, tert-butyllithium, phenyllithium, where the benzene ring may bear substituents at any position (e.g. OCH$_3$, CH$_2$NMe$_2$, CONR$_2$), cyclohexyllithium, where the cyclohexyl ring may comprise heteroatoms (e.g. O, N, S), ethyllithium, lithium pentadienyl, lithium 2-furanyl, lithium 2-thiophenyl, lithium ethynyl. Also suitable are sodium alkyl compounds, such as sodium cyclopentadienyl.

The suitable alkaline earth metal alkyls include magnesium alkyl compounds (Grignard reagents) of the general formula R$^1$MgX, where R$^1$ may be one of the radicals listed above and X may be F, Cl, Br, I.

The base can be used in a stoichiometric amount or in a superstoichiometric amount, based on the metallalactone. In some embodiments, the amount of base used per catalytic cycle may be 1 to 2, such as 1 to 1.1, equivalents based on the metallalactone.

In step c), the adduct is reacted with an alkene. The alkene displaces the alkali metal or alkaline earth metal salt of the α,β-ethylenically unsaturated carboxylic acid from the coordination site on the active metal. At the same time, the transition metal-alkene complex is regenerated and is available for a new catalytic cycle. This completes the catalytic cycle. The displaceability of the alkali metal or alkaline earth metal salt of the α,β-ethylenically unsaturated carboxylic acid from the adduct is surprising since the adduct of free acrylic acid with the transition metal complex IV' does not exhibit this reaction.

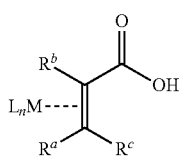

IV'

The initial formation of the transition metal-alkene complex (or the regeneration of the transition metal-alkene complex according to step c) in the second and further catalytic cycles) and step a) of the process can be performed separately from one another, by adding the alkene and $CO_2$ in succession or in spatial separation from one another. The initial formation (or the regeneration of the transition metal-alkene complex according to step c) in the second and further catalytic cycles) and step a) of the process can, however, also be performed essentially simultaneously, by adding the alkene and $CO_2$ simultaneously or adding a mixture of alkene and $CO_2$.

The $CO_2$ for use in the reaction can be used in gaseous, liquid or supercritical form. It is also possible to use carbon dioxide-comprising gas mixtures available on the industrial scale, provided that they are substantially free of carbon monoxide.

$CO_2$ and alkene may also comprise inert gases such as nitrogen or noble gases. Advantageously, however, the content thereof is below 10 mol %, based on the total amount of carbon dioxide and alkene in the reactor.

In the case of simultaneous addition of carbon dioxide to alkene (or addition of a mixture of $CO_2$ to alkene), the molar ratio of carbon dioxide to alkene in the feed is generally 0.1 to 10, such as 0.5 to 5.

It has been found that, surprisingly, suitable selection of the ligand L prevents the formation of a transition metal-$CO_2$ complex and rules out side reactions. Even in the presence of $CO_2$, the transition metal-alkene complex is the first to form with the alkene.

In one or more embodiments, the base is added separately from the addition of the $CO_2$ in order to prevent a direct reaction of the base with the $CO_2$. In these embodiments, the base is therefore added at a different time than the addition of the $CO_2$.

The reactors used may in principle be all reactors which are suitable in principle for gas/liquid reactions or liquid/liquid reactions at the given temperature and the given pressure. Suitable standard reactors for liquid-liquid reaction systems are specified, for example, in K. D. Henkel, "Reactor Types and Their Industrial Application", in Ullmann's Encyclopedia of Industrial Chemistry 2005, Wiley VCH Verlag GmbH & Co KGaA, DOI: 10.1002/14356007.b04_087, chapter 3.3 "Reactors for gas-liquid reactions". Examples include stirred tank reactors, tubular reactors or bubble columns.

In order to achieve good mixing of the reactants and of the medium comprising the carboxylation catalyst and the strong base, suitable apparatuses can be used. Such apparatuses may be mechanical stirrer apparatuses with one or more stirrers, with or without baffles, packed or nonpacked bubble columns, packed or nonpacked flow tubes with or without static mixers, or other useful apparatuses known to those skilled in the art for these process steps. The use of baffles and delay structures is explicitly included in the process according to the invention.

The reactor is filled with the reaction solvent and the transition metal precomplex, or alternatively the transition metal source and the ligand L. Subsequently, the alkene and, at the same time or a different time or a different place, $CO_2$ are injected. After the end of each addition step, the reactor can be decompressed. At a different time or place, the base is then added. The catalytic cycle can then be repeated once or more than once, alkene and, at the same time or a different time or a different place, $CO_2$ can be injected again, and base can be added at a different time or different place.

Such a spatial separation can be effected, for example, in a stirred tank simply by means of two or more separate inlets. When several tanks are used, it is possible, for example, for different media charges to be effected in different tanks. Separation of the times of addition of the alkene and $CO_2$ reactants on the one hand and the base reactant on the other hand is required in the process according to the invention. Such a time separation can be effected, for example in a stirred tank, by alternating the charging with the reactants. In the case of use of flow tubes or apparatuses of a similar kind, such charging can be effected, for example, at different sites in the flow tube; through such a variation in the addition sites, the reactants can be added as a function of residence time.

Steps a) to c) are performed may be in the liquid or supercritical phase at pressures between 1 and 150 bar, such as at pressures between 1 and 100 bar or between 1 and 60 bar. In some embodiments, steps a) to c) of the process may be performed at temperatures between −20° C. and 300° C., such as at temperatures between 20° C. and 250° C. or at temperatures between 40° C. and 200° C.

After one or more catalytic cycles, the alkali metal or alkaline earth metal salt of the α,β-ethylenically unsaturated carboxylic acid formed in step c) is separated from the reaction medium. For example, the alkali metal or alkaline earth metal salt of the α,β-ethylenically unsaturated carboxylic acid may be sparingly soluble in the reaction medium and precipitate, such that it can be separated by solid-liquid phase separation, such as removal by filtration, decantation or centrifugation.

The removal of the derivative may comprise a liquid-liquid phase separation into a first liquid phase in which the alkali metal or alkaline earth metal salt of the α,β-ethylenically unsaturated carboxylic acid is enriched, and a second liquid phase in which the transition metal-alkene complex is enriched. The second phase generally comprises the reaction solvent.

The use of effects which facilitate a separation, such as the change of phase of ionic liquids or of supercritical media, is explicitly included in the process. Change in pressures or temperatures which have a favorable effect on the separation of the phases are explicitly included in the process. The liquid-liquid extraction can be effected in all apparatuses suitable therefor, such as stirred vessels, extractors or percolators.

The liquid-liquid phase separation is supported by the additional use of a polar solvent in which the derivative of the alkali metal or alkaline earth metal salt of the α,β-ethylenically unsaturated carboxylic acid has good solubility, and which is immiscible or has only limited miscibility with the second liquid phase in which the transition metal-alkene complex is enriched. The polar solvent is generally selected by simple tests.

In one or more embodiments, separation of the alkali metal or alkaline earth metal salt of the α,β-ethylenically unsaturated carboxylic acid may be effected via the separation thereof into two different phases. It is thus possible, for example, to remove the alkali metal or alkaline earth metal salt of the α,β-ethylenically unsaturated carboxylic acid in a polar aqueous phase from the existing organic phase.

The remaining organic phase is recycled into step a). This recycling is undertaken under conditions which are favorable for the process.

The invention is illustrated in detail by the appended drawings and the examples which follow.

In the examples, the following abbreviations are used:
dtbpe 1,2-bis(di-tert-butylphosphino)ethane
$Ni(COD)_2$ bis(cyclooctadiene)nickel(0)
THF tetrahydrofuran
NaOtBu sodium tert-butoxide Example 1

Preparation of the (dtbpe)Ni(Ethylene) Complex

Figure 3:
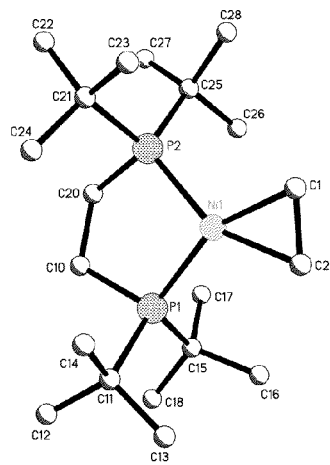
FIG. 3 shows the X-ray structure analysis of the (dtbpe)Ni (ethylene) complex.
Figure 4:
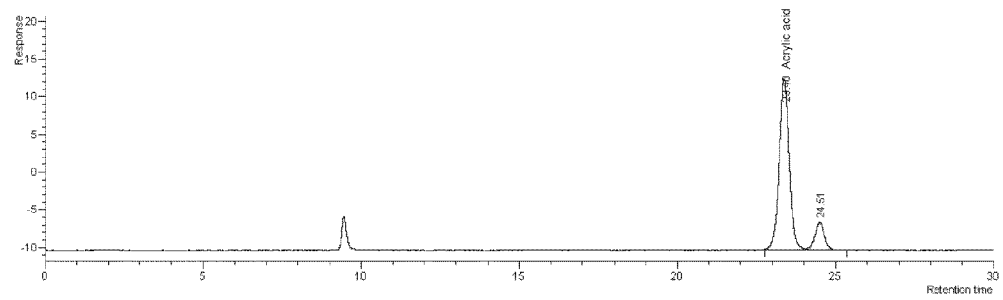
FIG. 4 shows the HPLC chromatogram of the reaction product from Example 7.

Under an argon atmosphere, dtbpe (662 mg, 2.1 mmol) and $Ni(COD)_2$ (571 mg, 2.1 mmol) were dissolved in THF (28 ml) and transferred to an autoclave. The autoclave was charged with ethylene (15 bar). After decompression, the solvent was removed to obtain 300 mg of yellow-brown crystals (36% yield). Crystals suitable for the X-ray structure analysis were obtained at −35° C. after addition of diethyl ether. The result of the X-ray structure analysis is shown in FIG. 3.

$C_{21}H_{44}NiO_2P_2$ (449.21) calc.: C, 59.28; H, 10.94; P, 15.29. found: C, 58.88; H, 10.85; P, 15.11. $^1$H NMR (500 MHz, $C_6D_6$): δ (ppm)=1.14 (m, 36H, $C(CH_3)_3$), 1.46 (m, 4H, $PCH_2CH_2P$), 2.42 (s, 4H, =$CH_2$). $^{13}C\{^1H\}$ NMR (126 MHz, $CD_2Cl_2$): δ (ppm)=24.2 (t, J=16.6 Hz, $PCH_2CH_2P$), 31.1 (t, J=3.3 Hz, $CH_3$), 34.3 (t, J=8.3 Hz, =$CH_2$), 34.7 (t, J=6.1 Hz, $C(CH_3)$). $^{31}P\{^1H\}$ NMR (81 MHz, $C_6D_6$): δ (ppm)= 105.2 (s). IR (KBr): 2944, 1663, 1477, 1387, 1364, 1179, 1163 $cm^{-1}$.

Example 2

Nickelalactone Formation

A suspension of dtbpe (159 mg, 0.5 mmol) and $Ni(COD)_2$ (138 mg, 0.5 mmol) in chlorobenzene (10 ml) was stirred until a red solution had formed. The mixture was transferred to an autoclave and diluted with chlorobenzene (10 ml). The autoclave was closed and filled with ethylene (20 bar). The mixture was stirred at room temperature (600 rpm) for 30 min, then the autoclave was decompressed down to a pressure of 10 bar and $CO_2$ was added up to a pressure of 50 bar. The mixture was heated to 45° C. and stirred for 16 h (600 rpm).

Figure 1:
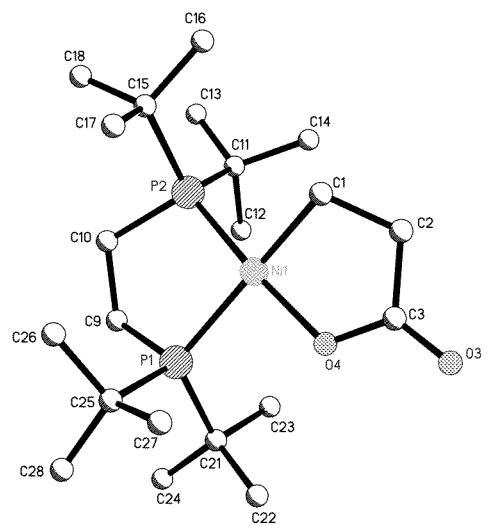
FIG. 1 shows the X-ray structure analysis of (dtbpe)nickela-γ-lactone.

After cooling to room temperature, the autoclave was opened, the solvent was removed and the residue was taken up in THF (3 ml). After additions of n-hexane (50 ml), a fine yellow precipitate formed, which was filtered off and dried under reduced pressure and corresponds to the title compound (164 mg, 73% yield). The result of the X-ray structure analysis is shown in FIG. 1.

Elemental analysis for $C_{21}H_{44}NiO_2P_2$ (449.21) calc.: C, 56.15; H, 9.87; P, 13.79. found: C, 54.80; H, 9.88; P, 13.32. $^1$H NMR (500 MHz, $C_6D_5Cl$): δ (ppm)=1.16-1.21 (m, 2H, Ni—$CH_2$), 1.37 (d, 18H, $C(CH_3)_3$, $J_{HP}$=12.5 Hz), 1.39 (d, 18H, $C(CH_3)_3$, $J_{HP}$=12.5 Hz), 1.46-1.54 (m, 2H, $CH_2CH_2$), 1.76-1.85 (m, 2H, $CH_2CH_2$), 2.04-2.09 (m, 2H, $CH_2$—COO). $^{13}C\{^1H\}$ NMR (126 MHz, $C_6D_5Cl$): δ (ppm)=9.6 (dd, J=62.9 Hz, J=26.4 Hz, Ni—$CH_2$), 18.4 (dd, J=14.9 Hz, J=9.1 Hz, $PCH_2CH_2P$), 26.2 (dd, J=39.3 Hz, J=22.1 Hz, $PCH_2CH_2P$), 30.2 (d, J=4.8 Hz, $C(CH_3)_3$), 30.3 (d, J=3.4 Hz, $C(CH_3)_3$), 34.6 (d, J=7.6 Hz, $C(CH_3)_3$), 36.4 (dd, J=17.8 Hz, J=1.9 Hz, $C(CH_3)_3$), 37.4 (dd, J=5.3 Hz, J=1.0 Hz, $CH_2COO$), 187.8 (s, J=17.3 Hz, COO). $^{31}P\{^1H\}$ NMR (81 MHz, $CD_2Cl_2$): δ (ppm)=77.8 (d, $J_{P,P}$=7.9 Hz), 80.6 ppm (d, $J_{P,P}$=8.9 Hz). HRMS (FAB+): m/z=449.2246 calc. for [M+H]: 449.2202. IR (KBr): 2994, 2953, 2899, 2866, 1627, 1481, 1468, 1313 $cm^{-1}$.

Example 2b

Nickelalactone Formation $Ni(COD)_2$ (14.4 mg, 52.3 μmol) and 3-tert-butyl-1-(di-tert-butylphosphinomethyl)-imidazol-2-ylidene (14.7 mg, 52.1 μmol) were dissolved in THF-$d_8$ (0.60 ml) and transferred to a high-pressure NMR tube. The tube was charged with ethylene (6 bar) and shaken at 40° C. for 6 h. The ethylene was decompressed and the tube was charged with $CO_2$ (8 bar). The solution was heated at 40° C. for 15 h. The corresponding nickelalactone was detected by spectroscopy.

$^1$H NMR (200 MHz, THF-$d_8$): δ (ppm)=0.74-0.84 (m, 2H, $NiCH_2CH_2COO$), 1.30-1.36 (d, $^3H_{PH}$=14 Hz, 18H, $((CH_3)_3)_2P$), 1.81 (s, 9H, $(CH_3)_3CN$), 1.89-1.98 (m, 2H, $NiCH_2CH_2COO$), 4.33 (d, J=4.0 Hz, $CH_2$), 7.12 (s, 1H, NCH=CHN), 7.25 (s, NCH=CHN). $^{13}C\{^1H\}$ NMR (50 MHz, THF-$d_8$): δ (ppm)=3.6 (d, J=30 Hz), 29.3 (d, J=3.3 Hz), 31.5 (s), 35.2 (d, J=17 Hz), 37.9 (s), 45.3 (d, J=24 Hz), 59.2 (s), 118.2 (d, J=5.2 Hz), 120.4 (s), 186.7 (s), 187.8 (d, J=9.0 Hz). $^{31}P\{^1H\}$ NMR (81 MHz, THF-$d_8$): δ (ppm)= 83.1 (s).

Example 2c

Nickelalactone Formation

A suspension of 2-(2-(diphenylphosphino)ethyl)pyridine (145.9 mg, 0.5 mmol) and $Ni(COD)_2$ (138 mg, 0.5 mmol) in THF (10 ml) was stirred until the solution turned red. The mixture was transferred to an autoclave and diluted with THF (10 ml). The autoclave was charged with ethylene (20 bar) and stirred at room temperature (600 rpm) for 30 minutes. Then the ethylene pressure was reduced (5 bar), and $CO_2$ was injected up to a final pressure of 45 bar. The mixture was stirred (600 rpm) at 45° C. for 24 h. After decompression and transfer to a glass vessel, the solvent was removed under reduced pressure and the residue was taken up in methanol (3 ml). When diethyl ether (50 ml) was added, a fine yellow solid precipitated out, which was found to be the corresponding nickelalactone, and was dried under high vacuum (148 mg, 68% yield).

$C_{23}H_{25}NNiO_2P$ (436.098) calc.: C, 62.60; H, 5.25; N, 3.32. found: C, 62.46; H, 5.35; P, 3.28. $^1$H NMR (200 MHz, $CD_2Cl_2$): δ (ppm)=0.43 (dd, 2H, J=16.4, J=7.2 Hz, Ni—$CH_2$), 2.14 (m, 4H, Ni—$CH_2$-$CH_2$, P—$CH_2$—$CH_2$), 3.28 (dd, 2H, J=26.3, J=4.7 Hz, P—$CH_2$), 7.07-8.01 (m, 13H), 9.08-9.13 (m, 1H). $^{31}$P{$^1$H} NMR (81 MHz, $CD_2Cl_2$): δ (ppm)=34.9. $^{13}$C{$^1$H} NMR (50 MHz, $CD_2Cl_2$): δ (ppm)= 8.89 (d, J=30.7 Hz), 24.4 (d, J=23.8 Hz), 33.6, 39.4, 121.8, 123.1, 124.8, 128, 129.2, 131.3, 133.3, 133.9, 136.7, 138.5, 149.5, 152.5. IR (KBr): 3850, 3433, 2924, 2902, 2880, 2859, 2792, 1629, 1603, 1479, 1446, 1434, 1404, 1161, 882, 861, 772, 747, 512 cm$^{-1}$.

Example 3

Nickelalactone Cleavage

A solution of the nickelalactone from example 2 (11.2 mg, 0.025 mmol) in chlorobenzene (1 ml) was admixed with NaOtBu (7.2 mg, 0.075 mmol) and stirred at room temperature for 1.5 h.

$^1$H NMR (200 MHz, $CD_3OD$): δ (ppm)=1.08-1.21 (m, 36H, $(CH_3)_3C$), 1.59-1.79 (m, 5H, $CH_2$, olefin CH), 2.10-2.22 (m, 1H, olefin CH), 2.75 (br, 1H, olefin CH). $^{31}$P{$^1$H} NMR (202 MHz, $CD_3OD$): δ (ppm)=87.3 (d, $^3J_{PP}$=61 Hz), 93.7 (d, $^3J_{PP}$=61 Hz).

Example 4 (Reference Example)

Preparation of a (dtbpe)Ni($η^2$-Acrylic Acid) Complex

Figure 2:
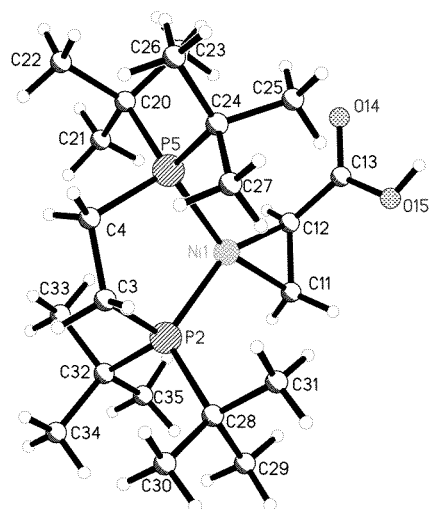
FIG. 2 shows the X-ray structure analysis of the (dtbpe)Ni ($\eta^2$-acrylic acid) complex.

Under an argon atmosphere, Ni(COD)$_2$ (1.50 g, 5.45 mmol) and dtbpe (1.74 g, 5.45 mmol) were dissolved in THF (20 ml). After cooling to 0° C., acrylic acid (0.39 ml, 5.7 mmol) was added gradually. The mixture was stirred at 0° C. for 3 h, the solvent was removed under reduced pressure and the residue was washed with diethyl ether (2×10 ml). Drying under reduced pressure gave the (dtbpe)Ni($η^2$-acrylic acid) complex (2.31 g, 94%) as a yellow powder. Crystals suitable for X-ray crystal structure analysis were obtained at room temperature by gradual diffusion of diethyl ether into a saturated THF solution. The result of the X-ray structure analysis is shown in FIG. 2.

$^1$H NMR (600 MHz, $C_6D_6$): δ=0.98 (d, $^3J_{PH}$=12 Hz, 9H, $(CH_3)_3C$), 1.10 (d, $^3J_{PH}$=12 Hz, 9H, $(CH_3)_3C$), 1.14 (d, $^3J_{PH}$=12 Hz, 9H, $(CH_3)_3C$), 1.22 (d, $^3J_{PH}$=12 Hz, 9H, $(CH_3)_3C$), 1.27-1.39 (m, 4H, $CH_2$), 2.26-2.27 (br m, 1H, CHH=$CHCO_2H$), 2.74-2.77 (br m, 1H, CHH=$CHCO_2H$), 3.36 (br m, 1H, CHH=$CHCO_2H$), 13.56 (br s, 1H, OH).

$^{13}$C{$^1$H} NMR (151 MHz, $C_6D_6$): δ=23.3-23.8 (m, $CH_2$), 30.3-30.6 (m, $(CH_3)_3C$), 33.0 (d, $^2J_{PC}$=23 Hz, $CH_2$=$CHCO_2H$), 34.4-34.7 (m, $(CH_3)_3C$), 35.3-35.4 (m, $(CH_3)_3C$), 42.7 (d, $^2J_{PC}$=14 Hz, $CH_2$=$CHCO_2H$), 182.7 (s, $CH_2$=$CHCO_2H$). $^{31}$P{$^1$H} NMR (243 MHz, $C_6D_6$): δ=86.1 (d, $^3J_{PP}$=53 Hz), 94.9 (d, $^3J_{PP}$=53 Hz). IR (KBr): 460, 631, 670, 712, 742, 817, 946, 991, 1019, 1114, 1138, 1196, 1272, 1366, 1428, 1474, 1567, 1641, 2358, 2870, 2903, 2953, 3469 cm$^{-1}$.

Example 5 (Reference Example)

Preparation of a (dtbpe)Ni($η^2$-Sodium Acrylate) Complex

Under an argon atmosphere, (dtbpe)Ni($η^2$-acrylic acid) (503 mg, 1.12 mmol) and sodium bis(trimethylsilyl)amide (209 mg, 1.12 mmol) were dissolved in THF (10 ml) and stirred at room temperature for 14 h. The yellow precipitate formed was filtered. Washing with THF gave the (dtbpe)Ni ($η^2$-sodium acrylate) complex (197 mg, 37%).

$^1$H NMR (600 MHz, $CD_3OD$): δ (ppm)=1.21-1.30 (m, 36H, $(CH_3)_3C$), 1.69-1.82 (m, 4H, $CH_2$), 1.88-1.89 (br m, 1H, CHH=$CHCO_2Na$), 2.27-2.28 (br m, 1H, CHH=$CHCO_2Na$), 2.86 (br m, 1H, $CH_2$=$CHCO_2Na$). $^{13}$C{$^1$H} NMR (151 MHz, $CD_3OD$): δ (ppm)=24.4-24.7 (m, $CH_2$), 30.9-31.4 (m, $(CH_3)_3C$), 35.0 (d, $^2J_{PC}$=22 Hz, $CH_2$=$CHCO_2Na$), 35.1-35.9 (m, $(CH_3)_3C$), 47.9 (d, $^2J_{PC}$=17 Hz, $CH_2$=$CHCO_2Na$), 187.3 (s, $CH_2$=$CHCO_2Na$). $^{31}$P{$^1$H} NMR (243 MHz, $CD_3OD$): δ (ppm)=87.2 (d, $^3J_{PP}$=61 Hz), 93.5 (d, $^3J_{PP}$=61 Hz). IR (KBr): 431, 454, 495, 529, 564, 578, 609, 664, 690, 792, 814, 838, 849, 899, 950, 989, 1022, 1055, 1095, 1140, 1180, 1279, 1367, 1392, 1452, 1479, 1561, 1637, 1659, 1685, 1908, 2718, 2867, 2900, 2948, 2979, 3041, 3085, 3407 cm$^{-1}$.

Example 6

Successful Ligand Exchange of (dtbpe)Ni($η^2$-Sodium Acrylate) Complex with Ethylene Under argon, the (dtbpe)Ni($η^2$-sodium acrylate) complex (32.4 mg, 72.1 μmol) from example 5 was dissolved in THF-d$_8$ (0.60 ml) and charged with ethylene (8 bar) in a high-pressure NMR tube. The reaction solution was heated at 60° C. for 20 h. NMR analysis showed the exclusive presence of the (dtbpe)Ni(ethylene) complex.

$^{31}$P{$^1$H} NMR (81 MHz, THF-d$_8$): δ (ppm)=35.9 (s) (dt-bpe, 4.1%), 91.9 (s) ((dtbpe)Ni(ethylene) complex, 95.9%). $^1$H NMR (200 MHz, THF-d$_8$): δ (ppm)=1.17-1.23 (m, 36H, $(CH_3)_3C$), 1.64-1.93 (br, 8H, $CH_2CH_2$ and olefin CH).

Example 7 (Inventive Example)

Catalytic Formation of Sodium Acrylate 1,2-bis(Di-tert-butylphosphino)ethane (79.5 mg, 0.25 mmol) and Ni(COD)$_2$ (69 mg, 0.25 mmol) were suspended in chlorobenzene (10 ml). The mixture was stirred until a red solution formed. The mixture was transferred to an autoclave and diluted with chlorobenzene (10 ml). The autoclave was charged with ethylene to 20 bar. The mixture was stirred (600 rpm) at 45° C. for 30 minutes. In step 1, the mixture was cooled to room temperature and the ethylene pressure was reduced to 10 bar. $CO_2$ was injected until a final pressure of 50 bar had been established. The mixture was stirred (600 rpm) at 60° C. for 2 h. The pressure was released, the mixture was cooled to room temperature, and the reactor was charged with ethylene (20 bar) and stirred for 1 min, in the course of which the pressure fell to 1 bar. This step was repeated three times. At ethylene pressure 1 bar, NaOtBu (48 mg, 0.5 mmol) was added to the mixture in step 2 and stirred for 1 h. The autoclave was charged with ethylene (20 bar), and the mixture was stirred at 45° C. for a further hour. After 18 cycles (steps 1 and 2), the pressure was released. $D_2O$ (46 ml) with Me$_4$I (25.1 mg, 0.125 mmol) was added as an internal standard. $^1$H NMR and HPLC analysis of the aqueous extract showed a superstoichiometric content of sodium acrylate (2.55 mmol, 1020% yield based on Ni(COD)$_2$).

$^1$H NMR (300 MHz, THF-d$_8$): δ (ppm)=1.24 (m, 36H, $C(CH_3)_3$), 1.65-1.85 (m, 4H, $CH_2$), 2.18 (m, 1H, olefin CH), 2.72 (br, 1H, olefin CH), 10.84 (br, 1H, COOH). $^{31}$P{$^1$H} NMR (81 MHz, $CD_2Cl_2$, 298 K), δ (ppm)=87.73 (d, $J_{P,P}$=55.56 Hz), 95.98 (d, $J_{P,P}$=55.56 Hz). HPLC (Shodex RSpak KC-811 300×8 mm (2 columns), 40° C., injection volume 100 μL, flow rate: 1 ml/min, detection: λ=205 nm, eluent: 0.1% phosphoric acid): 0.88% by weight of acrylic acid.

Example 8 (Comparative Example)

Attempted Ligand Exchange of (dtbpe)Ni($\eta^2$-Acrylic Acid) Complex with Ethylene Under argon, the (dtbpe)Ni($\eta^2$-acrylic acid) complex (31.5 mg, 70.1 μmol) was dissolved in THF-$d_8$ (0.60 ml) and introduced into a high-pressure NMR tube. The tube was charged with ethylene and stirred at 60° C. for 18 h. The NMR analysis showed the product to be a mixture of (dtbpe)Ni(ethylene) (3.1%), (dtbpe)Ni($\eta^2$-acrylic acid) (95.6%) and free dtbpe ligand (1.3%). $^{31}$P{$^1$H} NMR (81 MHz, THF-$d_8$): δ (ppm)= 36.0 (s, dtbpe), 86.8 (d, $^3J_{PP}$=55 Hz, (dtbpe)Ni($\eta^2$-sodium acrylate)), 91.9 (s, (dtbpe)Ni(ethylene)), 95.2 (d, $^3J_{PP}$=55 Hz, (dtbpe)Ni($\eta^2$-sodium acrylate)).

The invention claimed is:

1. A process for preparing an alkali metal or alkaline earth metal salt of an α,β-ethylenically unsaturated carboxylic acid, wherein
    a) a transition metal-alkene complex is reacted with $CO_2$ to give a metallalactone,
    b) the metallalactone is reacted with a base to give an adduct of an alkali metal or alkaline earth metal salt of an α,β-ethylenically unsaturated carboxylic acid with the transition metal complex, the base being selected from alkali metal or alkaline earth metal hydroxides and alkali metal or alkaline earth metal superbases, and
    c) the adduct is reacted with an alkene to release the alkali metal or alkaline earth metal salt of the α,β-ethylenically unsaturated carboxylic acid and regenerate the transition metal-alkene complex.

2. The process according to claim 1, wherein the alkali metal or alkaline earth metal superbase is selected from alkali metal or alkaline earth metal alkoxides, alkali metal or alkaline earth metal hydrides, alkali metal or alkaline earth metal azides, alkali metal or alkaline earth metal phosphides, alkali metal or alkaline earth metal silanolates, alkali metal or alkaline earth metal alkyls or alkali metal or alkaline earth metal aryls.

3. The process according to claim 1, wherein the transition metal complex comprises at least one metal of group 4, 6, 7, 8, 9 or 10 of the Periodic Table of the Elements.

4. The process according to claim 3, wherein the transition metal complex comprises a complex of Ni.

5. The process according to claim 1, wherein the transition metal complex comprises at least one ligand which comprises at least one phosphorus atom which coordinates to the transition metal and/or a carbene group which coordinates to the transition metal.

6. The process according to claim 5, wherein the ligand comprises at least one phosphorus atom which coordinates to the transition metal and at least one radical is bonded to the phosphorus atom via a secondary or tertiary carbon atom.

7. The process according to claim 5, wherein the ligand comprises a bidentate P,P, P,N, P,O or P,carbene ligand.

8. The process according to claim 7, wherein the bidentate P,P, P,N, P,O or P,carbene ligand is coordinated to the transition metal to form a five-membered ring.

9. The process according to claim 8, wherein the ligand comprises 1,2-bis(di-tert-butylphosphino)ethane or bis(di-tert-butylphosphino)methane.

10. The process according to claim 1, wherein the alkene comprises ethene and the α,β-ethylenically unsaturated carboxylic acid comprises acrylic acid.

11. The process according to claim 1, wherein the reaction medium comprises a solvent selected from aromatic hydrocarbons, halogenated aromatic hydrocarbons, ethers, alcohols, dimethylformamide, dimethyl sulfoxide, water and mixtures thereof.

12. The process according to claim 1, wherein the alkali metal or alkaline earth metal salt of the α,β-ethylenically unsaturated carboxylic acid formed in step c) is removed from the reaction medium.

13. The process according to claim 12, wherein the removal comprises a liquid-liquid phase separation into a first liquid phase in which the salt of the α,β-ethylenically unsaturated carboxylic acid is enriched, and a second liquid phase in which the transition metal-alkene complex is enriched.

14. The process according to claim 13, wherein, after step c), the reaction medium is extracted with an aqueous phase and the first liquid phase obtained is an aqueous solution of the alkali metal or alkaline earth metal salt of the α,β-ethylenically unsaturated carboxylic acid.

* * * * *